US011745022B2

(12) United States Patent
Julien et al.

(10) Patent No.: US 11,745,022 B2
(45) Date of Patent: Sep. 5, 2023

(54) IMPLANTABLE MEDICAL LEAD WITH STRAIN RELIEF DEVICE

(71) Applicant: SORIN CRM SAS, Clamart (FR)

(72) Inventors: Etienne Julien, Paris (FR); Nicolas Shan, Antony (FR); Maxime Rault, Paris (FR)

(73) Assignee: SORIN CRM SAS, Clamart (FR)

( * ) Notice: Subject to any disclaimer, the term of this patent is extended or adjusted under 35 U.S.C. 154(b) by 174 days.

(21) Appl. No.: 16/688,855

(22) Filed: Nov. 19, 2019

(65) Prior Publication Data

US 2020/0155856 A1    May 21, 2020

(30) Foreign Application Priority Data

Nov. 21, 2018    (FR) ........................................ 1871665

(51) Int. Cl.
*A61N 1/375* (2006.01)
*A61N 1/05* (2006.01)
*A61N 1/08* (2006.01)
*A61N 1/39* (2006.01)

(52) U.S. Cl.
CPC ......... *A61N 1/3752* (2013.01); *A61N 1/0563* (2013.01); *A61N 1/08* (2013.01); *A61N 1/3956* (2013.01)

(58) Field of Classification Search
None
See application file for complete search history.

(56) References Cited

U.S. PATENT DOCUMENTS

| | | | |
|---|---|---|---|
| 3,769,984 A | 11/1973 | Muench et al. | |
| 5,626,491 A * | 5/1997 | Hasircoglu | H01R 12/772 |
| | | | 439/459 |
| 5,984,711 A | 11/1999 | Woodard | |
| 6,293,594 B1 | 9/2001 | Safarevich et al. | |
| 6,697,675 B1 | 2/2004 | Safarevich et al. | |

(Continued)

FOREIGN PATENT DOCUMENTS

| | | |
|---|---|---|
| CN | 106232181 A | 12/2016 |
| CN | 108348747 A | 7/2018 |

(Continued)

OTHER PUBLICATIONS

Second office action issued in Chinese Application No. 201911147244.1 dated Sep. 3, 2021.

(Continued)

*Primary Examiner* — Erica S Lee (57) ABSTRACT

The present invention relates to an implantable lead comprising at least one conductive wire and a connector. The connector is configured to be connected to an implantable medical device, such as a cardiac stimulation, a defibrillation or/and a neuromodulation device, and further comprising a strain relief device extending longitudinally along an axis from one end of the connector and essentially parallel to the longitudinal axis of the connector. The conductive wire is deflected by a deflection wall of the strain relief device such that the deflection wall of the strain relief device blocks the conductive wire against the deflection wall when the conductive wire is stressed in tension, and the deflection wall extends along an axis which is misaligned with the longitudinal axis of the strain relief device.

14 Claims, 5 Drawing Sheets

(56) References Cited

U.S. PATENT DOCUMENTS

| | | | |
|---|---|---|---|
| 7,520,763 B1* | 4/2009 | Buse | H01R 31/06 439/121 |
| 7,680,544 B1 | 3/2010 | Conger | |
| 8,295,948 B2 | 10/2012 | Barker et al. | |
| 8,417,343 B2 | 4/2013 | Bolea et al. | |
| 8,939,905 B2 | 1/2015 | Schugt et al. | |
| 2004/0064174 A1 | 4/2004 | Belden | |
| 2005/0222634 A1 | 10/2005 | Flickinger et al. | |
| 2009/0018393 A1 | 1/2009 | Dick et al. | |
| 2010/0121421 A1* | 5/2010 | Duncan | A61N 1/05 607/116 |
| 2010/0179627 A1 | 7/2010 | Floyd et al. | |
| 2011/0009934 A1* | 1/2011 | Conger | A61N 1/05 607/116 |
| 2011/0022142 A1* | 1/2011 | Barker | A61N 1/0558 607/117 |
| 2011/0220408 A1 | 9/2011 | Walsh et al. | |
| 2011/0257659 A1 | 10/2011 | Mehdizadeh et al. | |
| 2012/0167385 A1 | 7/2012 | McGiboney et al. | |
| 2013/0005169 A1 | 1/2013 | Soltis et al. | |
| 2014/0058276 A1* | 2/2014 | Bodecker | A61B 5/0031 600/486 |
| 2015/0165217 A1 | 6/2015 | Hughes | |
| 2016/0158558 A1 | 6/2016 | Shanahan et al. | |
| 2016/0287862 A1 | 10/2016 | Shan et al. | |
| 2016/0296749 A1 | 10/2016 | Farr et al. | |
| 2018/0165217 A1 | 6/2018 | Greenspan | |

FOREIGN PATENT DOCUMENTS

| | | |
|---|---|---|
| EP | 1 426 079 | 6/2004 |
| EP | 2 571 569 | 3/2013 |
| EP | 3 075 411 A1 | 10/2016 |
| WO | WO-2011/145084 | 11/2011 |
| WO | WO-2017/191507 | 11/2017 |

OTHER PUBLICATIONS

Office Action on JP Application No. 2019-202509 dated Jan. 18, 2021.

Office Action on JP Application No. 2019-202510 dated Jan. 18, 2021.

French Search Report for French Application No. 1871664 dated Sep. 11, 2019, 1 page.

French Search Report for French Application No. 1871665 dated Sep. 9, 2019, 2 pages.

First office action on Chinese Application No. 201911147244.1 dated Nov. 2, 2020. 14 pages.

* cited by examiner

IMPLANTABLE MEDICAL LEAD WITH STRAIN RELIEF DEVICE

CROSS-REFERENCE TO RELATED APPLICATION

This application claims the benefit of and priority to French Application No. 1871665, filed Nov. 21, 2018, which is incorporated herein by reference in its entirety.

BACKGROUND

The present invention relates to an implantable medical lead comprising a strain relief device, as well as to a lead connector and to a method of manufacturing such an implantable lead.

Implantable medical leads are commonly used in combination with implantable medical devices, such as cardiac pacing, defibrillation, and/or neuromodulation devices.

In order, for example, to deliver electrical stimulation to a patient, an implantable lead comprises one or more electrodes that are implanted in the heart of the patient. Conductive wires housed within the implantable lead electrically couple the electrode(s) to a connector of the lead, which is coupled to the implantable medical device. Thus, the device can detect cardiac electrical activity and/or deliver a suitable electrical therapy by means of the one or more electrodes of the lead electrically connected to the device.

The electrical connection between the conductive wires and the connector of the lead, made by welding, for example, is likely to be mechanically stressed, especially during the implantation of the lead, and during the life of the patient. It is then necessary for the conductive wires, in particular those whose diameter is less than 200 micrometers, to withstand such mechanical stresses, especially in tension, in order to avoid a break in the electrical connection with the connector or of the conductive wire.

It is known from US 2013/0005169 A1 to place a flexible tube of biocompatible material around the implantable lead body to reduce strain relief stresses at the distal end of the lead. Document US 2011/0257659 A1 also describes a flexible tube-shaped strain relief device into which the lead is introduced. However, these strain relief devices are additional elements to the lead that are brought into direct contact with the heart tissue, which is preferable to avoid reducing the risk of contamination.

U.S. Pat. No. 7,680,544 B1 discloses a lead comprising a strain relief device housed in a segment of the lead outside the housing of the implantable medical device. This device comprises a structure whose elements (85a, 85b, 85c) extend radially with respect to the tubular body of the lead such that conductive cables are wound helically around the tubular body of the lead. As a result, in addition to occupying more space in order to distribute the radially extending elements (85a, 85b, 85c), the lead described by U.S. Pat. No. 7,680,544 B1 is not adapted to absorb strong constraints which are transmitted to the welding between the connector and the wires.

SUMMARY

The object of the present invention is thus to improve the tensile strength of the conductive wire of an implantable lead, in order to secure and maintain the electrical connection of the conductive wire to the connector of the lead.

The object of the present invention is achieved with an implantable lead comprising at least one conductive wire and a connector configured to be connected to an implantable medical device such as a cardiac stimulation device, a defibrillation device and/or a neuromodulation device, and further comprising a strain relief device which extends longitudinally along an axis from one end of the connector and essentially parallel to the longitudinal axis of the connector and which a deflection wall, such that the conductive wire is deflected by the deflecting wall of the strain relief device so that the strain relief device blocks the conductive wire against the deflection wall when the conductive wire is stressed in tension, and the deflection surface extends along an axis which is misaligned with the longitudinal axis of the strain relief device. The arrangement of the conductive wire around the strain relief device enables the conductive wire to be deflected in a non-radial manner about the longitudinal axis of the strain relief device by means of the deflection wall such that the conducting wire is hangs on the deflection wall when the conductive wire is stressed in tension. The advantage of blocking the conductive wire on the deflection wall is that it prevents the entire length of the conductive wire from being axially solicited by tension force. As a result, the arrangement of the conductive wire around the device reduces the tension experienced by the lead. In addition, the deviation of the conductive wire by the deflection wall, the axis of which is misaligned with the longitudinal axis of the strain relief device, makes it possible to shorten the necessary distance for arranging the conductive wire around the strain relief device, in particular in comparison with tubular devices around which the conductive wire is radially wound, that is to say helically around the longitudinal axis of the device. Consequently, the deflection of the conductive wire by the deflection wall of the strain relief device makes it possible to reduce the mechanical stresses to which the conductive wire is subjected in tension and thus to reduce the risk of rupture of the conductive wire itself and at the level of the electrical connection with the lead connector. As a result, the strain relief device makes it possible to improve the reliability and the longevity of the electrical connection between the conductive wire and the lead connector.

The implantable lead according to the present invention can be further improved with the following embodiments.

According to another embodiment of the invention, the strain relief device may comprise a through hole and/or a notch whose depth extends along an axis misaligned with the longitudinal axis of the strain relief device, and/or a protrusion that extends from the strain relief device along an axis misaligned with the longitudinal axis of the strain relief device. The strain relief device thus comprises deflection walls for deflecting the conductive wire, that is to say at least partially preventing a helical winding of the conductive wire around the longitudinal axis of the device, which reduces the length of the device necessary for the strain relief.

According to another embodiment of the invention, at least one section of the conductive wire may be arranged in a loop around the deflection wall of a protuberance which projects from an outer surface of the strain relief device. Thus, the protuberance provides a stop means to the conductive wire when it is arranged in a loop around the wall of the protuberance.

According to another embodiment of the invention, the protuberance may have a cylindrical shape and an axis of revolution misaligned with the longitudinal axis of the strain relief device. The cylindrical structure of the protuberance facilitates the arrangement of the conductive wire around the protrusion from its circular cross section and avoids the presence of sharp edges or edges that could damage the conductive wire, especially when it hangs on the wall of the protrusion in response to a stress in tension.

According to another embodiment of the invention, the conductive wire may be introduced at least two times through the through hole so that the lead is arranged in a loop around a portion of the strain relief device. The through hole thus provides a means of stopping the conductive wire when the latter is arranged in loop around the walls of the through hole.

According to another embodiment of the invention, the deflection wall may extend along an axis which is misaligned with the longitudinal axis of the strain relief device so as to form an essentially straight angle, in particular a right angle at plus or minus 10 degrees. As a result, the deflection wall deflects the conductive wire so that the conductive wire is not arranged radially around the longitudinal axis of the strain relief device at least over a portion of the strain relief device. The non-radial arrangement of the conductive wire makes it possible to improve the retention of the conductive wire to the strain relief device and to increase the capacitance of the conductive wire to absorb tension stresses.

According to another embodiment of the invention, at least two sections of the conductive wire may overlap and/or be superimposed. Thus, the friction between sections of the conductive wire and with the strain relief device is increased which contributes to preventing a tension force applied to the wire can undo the arrangement of the conductive wire around the strain relief device.

According to another embodiment of the invention, the connector and the strain relief device may each be provided with one or more lumens; at least one lumen of the strain relief device being aligned with a lumen of the connector. As a result, the strain relief device is adapted for an implantable lead whose connector is provided with one or more lumens.

According to another embodiment of the invention, the implantable lead may comprise a plurality of conductive wires such that each conductive wire is deflected by the strain relief device so that the strain relief device blocks the conductive wires when the conductive wires are stressed.

According to another embodiment of the invention, the conductive wires can exit from one end of the connector separately from each other and are grouped into a multi-strand wire by their arrangement around the strain relief device. Thereby, in addition to improving the tension resistance of the conductive wires by their deflection caused by the deflection wall, the strain relief device also simplifies the arrangement of the conductive wire by joining them in a single multi-strand wire.

According to another embodiment of the invention, the strain relief device can be attached to one end of the connector by gluing, by interlocking, by snap connection and/or by one or more fasteners. The strain relief device of is easily attached to the connector.

Alternatively, the strain relief device and the at least one deflection wall can be formed integrally with the connector. In this method, the number of components is reduced, which reduces costs and avoids an assembly step for fixing the strain relief device to the connector.

The object of the present invention is also achieved with an implantable medical device such as a cardiac stimulation device, a defibrillation device and/or a neuromodulation device comprising an implantable lead, itself comprising a connector, a strain relief device of longitudinal axis and at least one conductive wire electrically connected to the connector. The strain relief device extends longitudinally from one end of the connector along an axis and is essentially parallel to the longitudinal axis of the connector, and comprises a deflection wall. The connector and the strain relief device are configured to be housed in the implantable medical device such that the conductive wire is deflected by the deflecting wall of the strain relief device so that the deflection wall of the strain relief device blocks the conductive wire when the conductive wire is stressed in tension, and the deflection wall member extends along an axis which is misaligned with the longitudinal axis of the strain relief device. The advantage of the blocking of the conductive wire on the deflection wall is that it prevents the entire length of the conductive wire from being axially stressed in tension. As a result, the arrangement of the conductive wire around the device makes it possible to reduce the tension experienced by the conductive wire. In addition, the deflection of the conductive wire by the deflection wall allows deflection in a non-radial manner of the conductive wire around the longitudinal axis of the strain relief device. This configuration, in comparison with tubular devices around which the conductive wire is wound radially, that is to say helically around the longitudinal axis of the device, improves the implementation and the holding of the conductive wire around the strain relief device and improves its ability to absorb stress in tension. Finally, the fact that the strain relief device is positioned inside the implantable medical device allows avoiding that the strain relief device, once implanted, is in direct contact with the tissues of the patient, and thus to limit the risk of contamination—especially of blood.

In addition, the object of the present invention is also achieved with a method of manufacturing an implantable lead configured to be connected by one or more conductive wires and a connector to an implantable medical device such as a cardiac stimulation device, a defibrillation device, and/or a neuromodulation device, the implantable lead further comprising a longitudinal axis strain relief device provided at one end of the connector, the strain relief device including a deflection wall. The method comprises a step of deflecting the conductive wire(s) by the strain relief device so as to arrange the conductive wire(s) of the connector around the deflection wall which extends along an axis which is misaligned with the longitudinal axis the strain relief device, so that when the conductor wire(s) are stressed in tension, the conductive wire(s) lock against the deflecting wall of the strain relief device. This method makes it possible to reduce the mechanical tension stresses to which the conductive wire is subjected because arranging and deflecting the lead around the strain relief device allows the conductive wire to lock on the deflection wall when it is stressed in tension. Consequently, the arrangement and the deflection of the conductive wire around the strain relief device makes it possible to reduce the risk of breakage of the conductive wire itself and at the electrical connection with the lead connector. Therefore, the strain relief device also improves the reliability and longevity of the electrical connection between the conductive wire and the connector of the lead. Indeed, this configuration, in comparison with tubular devices around which the conductive wire is wound radially, that is to say helically around the longitudinal axis of the device, improves the implementation and the holding the lead around the strain relief device and improves its ability to absorb stress in tension.

The various embodiments can be combined to form more variants of advantageous embodiments of the present invention.

BRIEF DESCRIPTION OF THE DRAWINGS

The invention and its advantages will be explained in more detail in the following by means of preferred embodiments and relying in particular on the figures.

Following examples, in which.

DETAILED DESCRIPTION

The invention will now be described in more detail using advantageous embodiments in an exemplary method and with reference to the drawings. The described embodiments are merely possible configurations and it should be borne in mind that the individual characteristics as described above can be provided independently of one another or can be omitted altogether during the implementation of the present invention.

Figure 1:
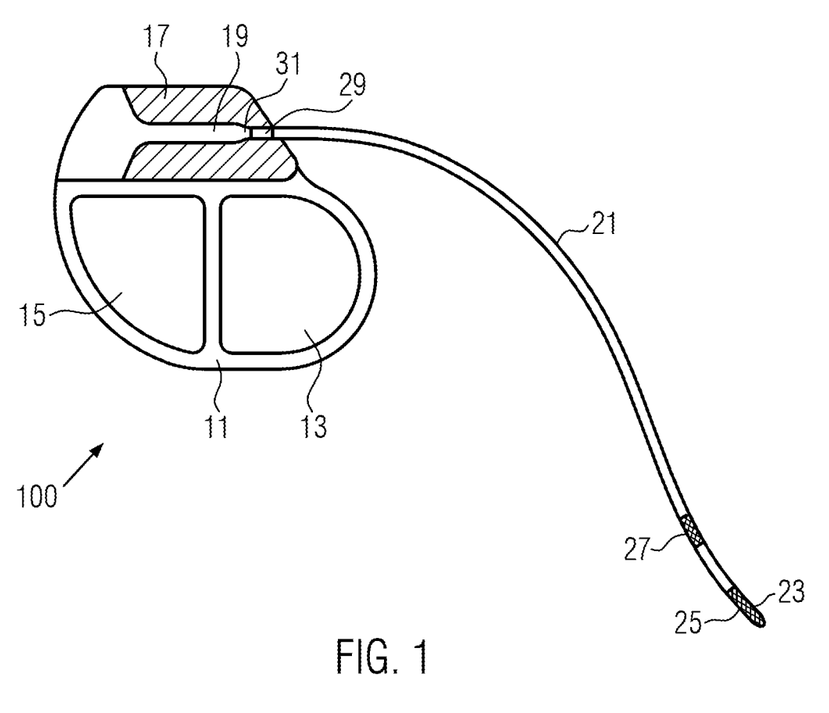
FIG. 1 schematically represents an implantable medical device provided with an implantable lead.

FIG. 1 schematically illustrates an implantable medical device 100 such as a cardiac stimulation device, a defibrillation device or/and a neuromodulation device. The implantable medical device 100 is provided with a metal housing 11, which comprises an electric circuit 13 and a battery 15, in particular a lithium battery. The implantable medical device 100 also comprises a plastic connection block 17 in which is housed an implantable lead connector 21. The connector 19 may be made from biocompatible conductive materials such as 316L stainless steel or a metal alloy, MP35N, for example. The material of the connector 19 may be selected for being biocompatible, as well as for conducting and transmitting appropriately electrical signals from the electrical stimulation device 100. Indeed, the connector 19 serves as a connection point between the implantable medical device 100 and the implantable lead 21. The implantable lead 21, of which a distal end 23 is provided with one or more electrodes and/or sensors 25, 27 able to be implanted in the heart of the patient, comprises conductive wires (not shown in FIG. 1) housed inside the implantable lead 21. These conductive wires make it possible to electrically couple the electrodes and/or sensors 25, 27 to the connector 19 of the lead 21 which is itself coupled to the implantable medical device 100. Thus, the device 100 can detect a cardiac electrical activity and/or deliver a suitable electrical therapy by means of the electrodes and/or sensors 25, 27 of the lead 21.

The implantable lead 21 is electrically connected to the implantable medical device 100 by means of a connection between the conductive wire of the lead 21 and the connector 19, made by welding, for example. In order to protect and maintain this electrical connection, especially when the wires of the lead 21 are stressed in tension during the implantation of the device 100 and during the life of the patient, a strain relief device 29 is attached to one proximal end 31 of the connector 19 housed in the connection block 17. Thus, the strain relief device 29 is positioned inside the implantable medical device 100, which makes it possible to prevent the strain relief device 29 from being in direct contact with the patient's tissues, and thus to limit the risk of contamination—in particular of the blood. In addition, the fact that the strain relief device 29 is housed in the connection block 17 with the connector 19 makes it possible to reduce the number of manipulations of the surgeon during the implantation of the device 100 in the body of a patient or patient or during replacement of the lead 21, in comparison with strain relief devices known in the state of the art and which are arranged around the lead outside the connection block and the connector.

The strain relief device 29 will now be further described in the following according to several embodiments of the present invention. Thus, each of the strain relief devices 200, 300, 400, 500, 600, 700, 800, 900 which will be described below is configured for the implantable lead 21 described in FIG. 1.

The elements, in particular relating to the lead connector, with the same numerical references already used for the description of FIG. 1 will not be described again in detail, and reference is made to their descriptions above.

Figure 2:
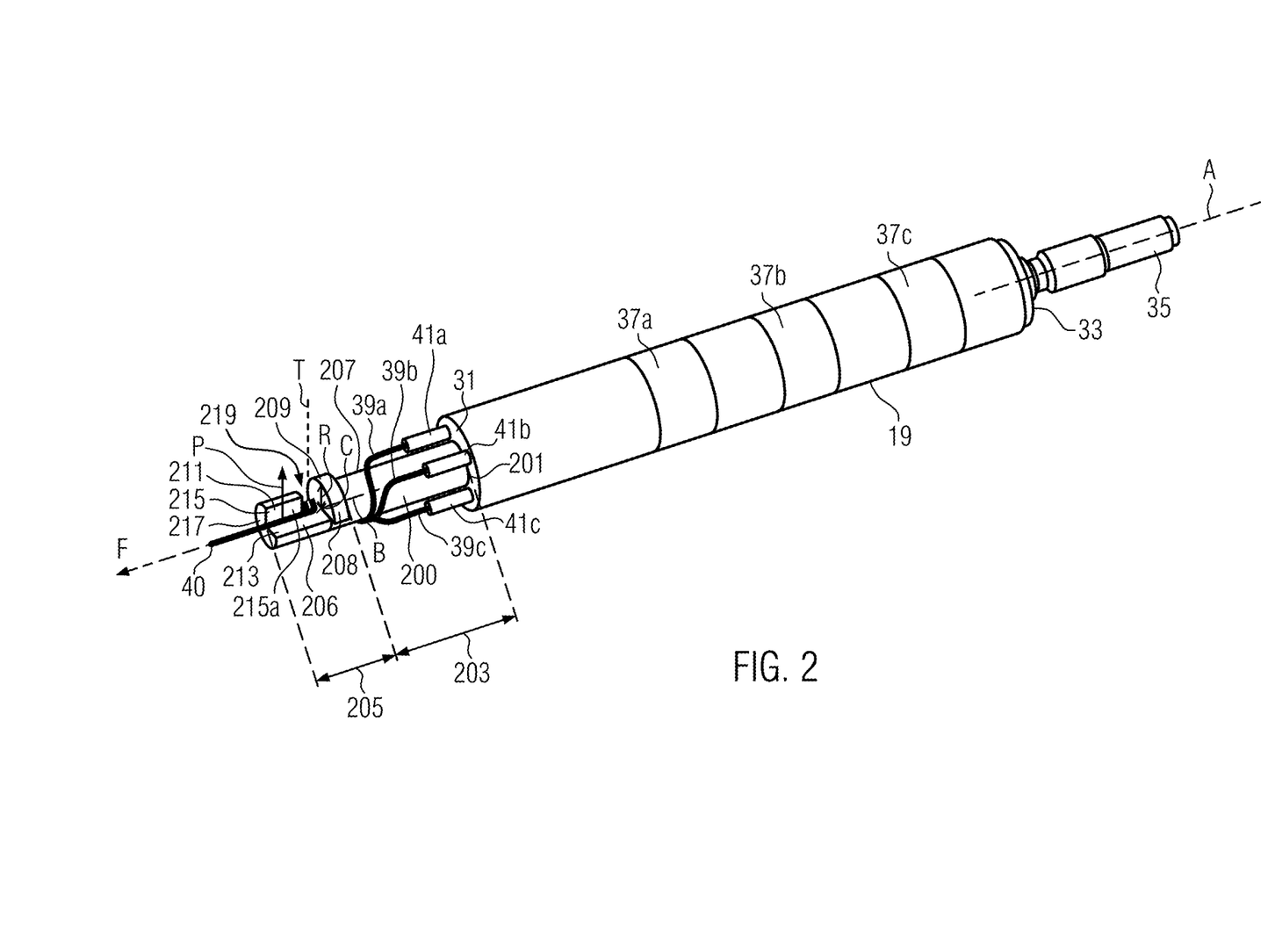
FIG. 2 represents a connector and a strain relief device according to a first embodiment of the present invention.

FIG. 2 illustrates the connector 19 and a strain relief device 200 according to a first embodiment of the present invention.

The connector 19 has a cylindrical shape of axis A and comprises at its distal end 33 a distal pin 35 configured to be connected to the connection block 17 of the implantable medical device 100 shown in FIG. 1.

The connector 19 shown in FIG. 2 is a multipolar connector because it is provided with three contacts 37a, 37b, 37c. In a variant, the connector 19 may comprise more or less than three contacts. In another variant, the connector 19 may comprise a single contact.

The implantable lead 21 comprises conductive wires 39a, 39b, 39c, electrically isolated from each other, which electrically connect the contacts 37a, 37b, 37c of the connector 19 to the electrodes 25, 27 (see FIG.1) of the lead 21. The conductive wires 39a, 39b, 39c are thus each housed and welded to a respective metal hypotube 41a, 41b, 41c of the connector 19 at the proximal end 31 of the connector 19. In a variant, the lead 21 may comprise more or less than three wires. In another variant, several conductive wires may be housed and welded to the same hypotube of the connector.

A risk of rupture of the electrical connection between the conductive wires 39a, 39b, 39c and the connector 19 of the lead 21, made by welding in the embodiment illustrated in FIG. 2, can be reduced by means of the strain relief device 200 according to the invention.

According to the first embodiment of the invention, the strain relief device 200 has an elongated shape and an end 201 which is attached to the proximal end 31 of the connector 19. For example, the strain relief device 200 can be attached to the proximal end 31 of the connector 19 by gluing, interlocking, snap connection or/and by one or more fixing elements.

Alternatively, the strain relief device 200 is formed integrally with the connector 19 to reduce the number of loose parts to assemble and facilitate the assembly of the connector 19.

The strain relief device 200 comprises a first portion 203 provided with the end 201 attached to the connector 19. The portion 203 has a cylindrical shape of circular cross section such that the cross section at any point of the portion 203 is smaller than the cross section at any point of the connector 19. In this way, the strain relief device 200 has a transverse dimension adapted to be attached to the proximal end 31 of the connector 19 between the hypotubes 41a, 41b, 41c which also protrude from the proximal end 31 of the connector 19.

The strain relief device 200 comprises a second portion 205 comprising a semi-cylinder shape with a full section 206 cut along its axis of revolution B which is aligned with the longitudinal axis A of the connector 19.

The second portion 205 is provided with a notch 219 formed between a first stop means 209 and a second stop means 211, whose depth T of the notch 219 extends perpendicularly to the axis of revolution B of the semi-cylinder 206.

Thus, the axis which extends along the depth T of the notch 219 and the axis of revolution B of the strain relief device are misaligned with respect to each other.

According to the first embodiment, the notch 219 constitutes a deflection element of the strain relief device 200 so that this deflection element 219 extends along the axis T which is misaligned with the longitudinal axis B of the strain relief device 200.

The first stop means 209, is here in the form of a half-disc 208 whose radius R is greater than that of the first cylindrical portion 203 and whose center C is positioned on the axis of revolution B. The first stop means 209 is positioned at a junction 207 between the first 203 and the second portion 205 of the strain relief device 200 so that the diameter of the planar section (not visible in FIG. 2) of the half-disk 208 is essentially perpendicular to the axis of revolution B of the semi-cylinder 206.

The second stop means 211 protrudes from the flat surface 213 of the semi-cylinder 106 in a direction P which is perpendicular to the axis B of the strain relief device 200. Here, the second stop means 211 a deflection wall 215. The angle 215a of the deflection wall 215 of the second stop means 211 on the notch side 219 is rounded so as not to damage the conductive wires 39a, 39b, 39c when are locked against the deflection wall 215 under the effect of a stress load of a force F.

To do this, the conductive wires 39a, 39b, 39c exit from their respective hypotubes 41a, 41b, 41c, to which they are welded, at the proximal end 31 of the connector 19 and are inserted into the notch 219 then deflected by the deflection wall 215a of the stop means 211, which constitutes a deflection element of the strain relief device 200.

The arrangement of the conductive wires 39a, 39b, 39c with respect to the notch 219 and the first and second stop means 209, 211 of the strain relief device 200 allows the conductive wires 39a, 39b, 39c to be able to be blocked against the deflection wall 215 when they are stressed in tension, that is to say that when the conductive wires 39a, 39b, 39c are stressed in tension by a force represented by an arrow F, they are locked on the strain relief device 200 at the deflection wall 215. This makes it possible in particular to reduce the mechanical stresses incurred by the conductors 39a, 39b, 39c in tension and thus reduce the risk of rupture of the conductive wires 39a, 39b, 39c themselves and at the electrical connection with the hypotubes 41a, 41b, 41c of the connector 19 of lead 21.

According to a second embodiment, not shown in FIG. 2, the conductive wires 39a, 39b, 39c are inserted through the notch 219 and then wound at least once around the second stop means 211 in order to avoid unintentional sliding of the conductive wires 39a, 39b, 39c outside the surface 213 of the semi-cylinder 206.

Figure 3:
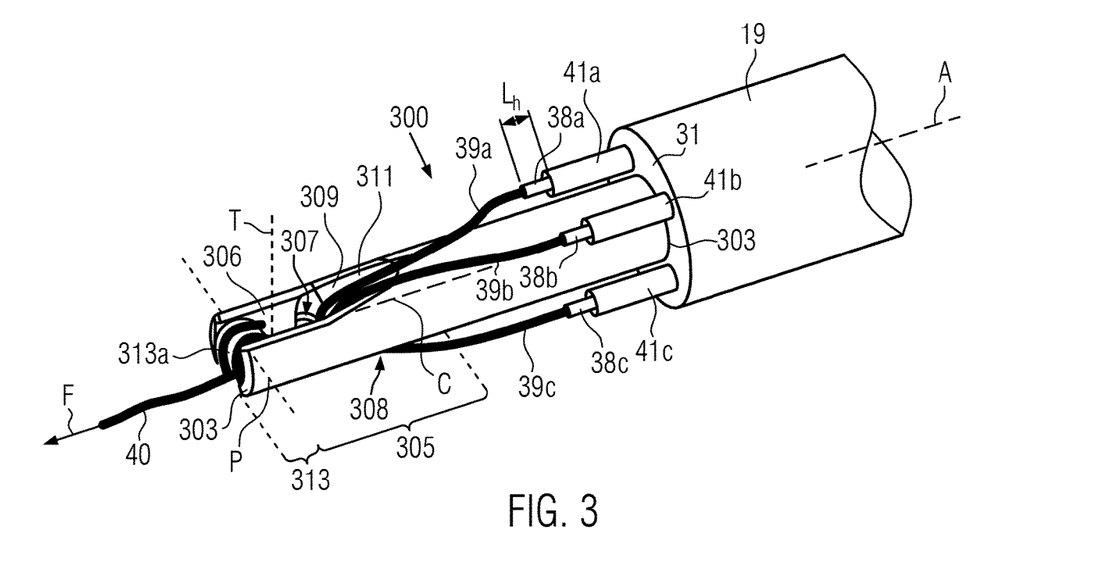
FIG. 3 shows a portion of the connector and a strain relief device according to a third embodiment of the present invention.

FIG. 3 illustrates a portion of the connector 19 and a strain relief device 300 according to a third embodiment of the present invention. The elements, in particular relating to the lead connector, with the same numerical references already used for the description of FIGS. 1 and 2 will not be described again in detail, and reference is made to their descriptions above.

The strain relief device 300 of FIG. 3 according to the third embodiment has an elongated cylindrical shape with an axis C and an end 301 which is attached to the proximal end 31 of the connector 19 as well as a second end 303 opposite the end 301.

According to the third embodiment, the conductive wire 39a is housed and welded to an intermediate hypotube 38a and the intermediate hypotube 38a is itself housed and welded in the hypotube 41a of the connector 19 at the proximal end 31 of the connector 19.

A laser welding of the conductive wire 39a to the intermediate hypotube 38a electrically connect the latter to the conductor wire 39a. The intermediate hypotube 38a is housed and welded by laser welding with the corresponding hypotube 41a so that a portion of length 1 h of the intermediate hypotube 38a protrudes out of the hypotube 41a and such that the intermediate hypotube 38a is electrically connected with the hypotube 41a. This weld between the intermediate hypotube 38a and the hypotube 41a is made outside the connector 19 which facilitates the realization of the welding between these two hypotubes 38a, 41a by providing more space and visibility to an operator for performing the laser welding.

The welding between the conductive wire 39a and the intermediate hypotube 39a, as well as the welding of the hypotubes 39a, 41a, are performed by laser welding. Laser welding makes it possible to produce a sealed weld, and also allows a weld particularly suitable at the connector scale of implantable leads of medical devices.

Thus, the intermediate hypotube 38a serves as an intermediate to the electrical connection between the conductive wire 39a and the hypotube 41a of the connector 19. The use of the intermediate hypotube 38a then makes possible an electrical connection between a connector 19 comprising a hypotube 41a, 41b, 41c with standard dimensions between 350 and 500 micrometers and a conductive wire 31a, 39b, 39c of diameter less than 150 micrometers.

The number of hypotubes, the number of intermediate hypotubes and the number of conductive wires are not limited to the illustration of FIG. 3. Thus, each hypotube 41a, 41b, 41c could each comprise an intermediate hypotube in which each conductive wire 39a, 39b, 39c would be housed, welded and electrically connected. In a variant, several conductive wires may be housed in the same intermediate hypotube.

A portion 305 of the strain relief device 300 towards the free end 303 comprises a first deflection element, here a through hole 307 whose depth extends along an axis T. Preferably, the hole 307 penetrates through the portion 305 of elongated cylindrical shape such that there is an intersection between the axis T of the through hole 307 and the axis C of the elongate cylindrical shape. As a result, the T axis and the C axis are misaligned with each other. The through hole 307 is dimensioned so that the conductive wires 39a, 39b, 39c can be inserted at either side of the hole 307 as shown in FIG. 3, or all inserted on the same side into the through hole 307. In addition, the inner periphery 309 of the through hole 307 facing the end 301 of the strain relief device 300 is chamfered or rounded to create a slope 311 which decreases toward the hole 307. The soft transition provided by the slope 311 at the area where the conductive wires 39a, 39b, 39c are introduced into the hole 307 reduces the risk of damaging the conductor wires 39a, 39b, 39c. In FIG. 3 only one inlet 306 of the through hole 307 is visible, the one including the chamfered perimeter 309. The other inlet 308, or outlet 308, opposite the inlet 306 of the through hole 307, is also provided with a chamfered or rounded contour.

The through hole 307 is defined on the side of the free end 303 of the strain relief device 300 by a portion 313. Thus, the portion 313 is between the end 303 and the through hole 307. This portion 313 is configured so that the conductive wires 39a, 39b, 39c, having been introduced into the through hole 307, are wound around the portion 313. The portion 313 is essentially cylindrical with an axis of revolution P perpendicular to the axis C of the strain relief device 300. The wall 313a of the portion 313 is a deflecting wall of the strain relief device 300.

According to the third embodiment, the conductive wires 39a, 39b are inserted through the inlet 306 into the through hole 307 and emerge through the other inlet 308, and are then wound at least once around the deflection wall 313a of the portion 313 along the axis P. The conductive wire 39c, meanwhile, is inserted through the inlet 308 into the through hole 307 and exits through the inlet 306, then is wound at least once in the direction contrary of the conductive wires 39a, 39b around the deflection wall 313a of the portion 313 along the axis P. According to one variant, the conductive wires 39a, 39b, 39c may be wound up several times around the deflection wall 313a of portion 313. Thus, the conductor wires 39a, 39b, 39c are grouped into a multi-strand wire 40 at the end 303 of the strain relief device 300.

As a result, the conductive wires 39a, 39b, 39c are deflected by the through hole 307 which forms a portion 313 whose deflection wall 313a blocks the conductive wires 39a, 39b, 39c when they are stressed in tension. The respective axes T, P of the deflection elements 307, 313 extend perpendicular to the longitudinal axis C of the strain relief device 300.

Therefore, if the multi-strand wire 40 is pulled by a tensile force F, during the implantation of the lead for example, the conductive wires 39a, 39b, 39c block against the deflection wall 313a of the strain relief device 300 which allows protecting them from the stress in tension. This also prevents the conductive wires 39a, 39b, 39c are drawn at the connection with the intermediate hypotubes 38a, 38b, 38c and the hypotubes 41a, 41b, 41c, which could break the weld between the conductive wires and the hypotubes and thus damage the electrical connection.

According to one variant, all the conductive wires 39a, 39b, 39c can pass through the hole 307 in the same direction, either through the inlet 306 or else through the inlet 308.

Figure 4:
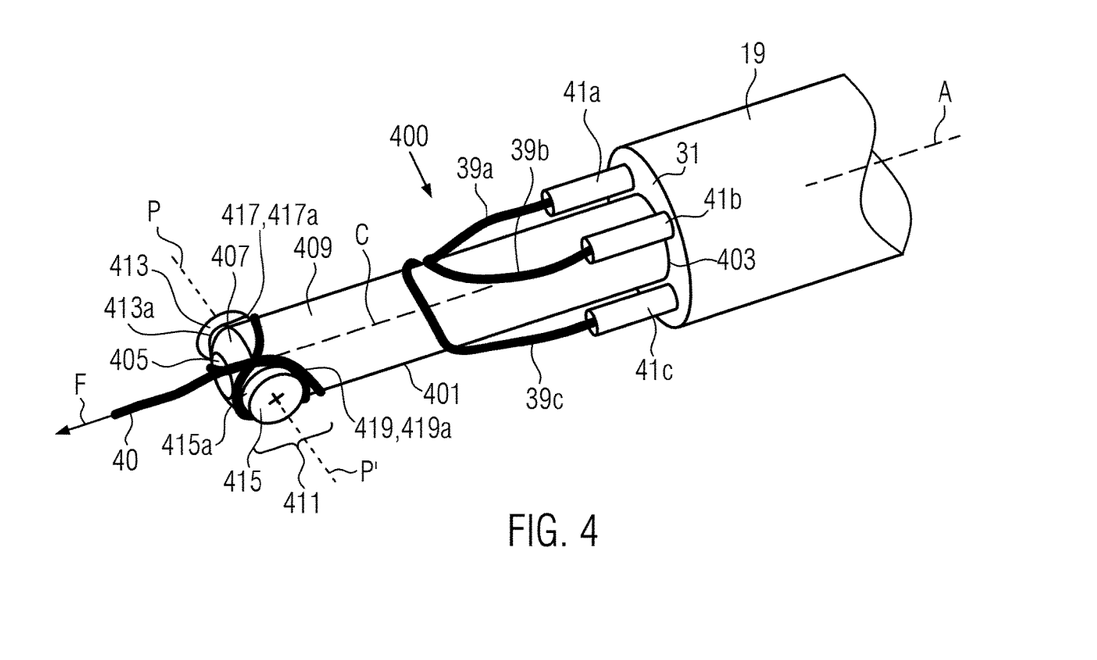
FIG. 4 represents a portion of the connector and a strain relief device according to a fourth embodiment of the present invention.

FIG. 4 illustrates a portion of the connector 19 and a strain relief device 400 according to a fourth embodiment of the present invention. The elements, in particular relating to the lead connector, with the same numerical references already used for the description of FIGS. 1 to 3 will not be described again in detail, and reference is made to their descriptions above.

The strain relief device 400 of FIG. 4 according to the fourth embodiment has a shape of a right circular cylinder 401 of axis of revolution C. A first end 403 of the cylinder 401 is attached to the proximal end 31 of the connector 19. A second end 405 of the cylinder 401, opposite the end 403, is shown as a free end 405 in FIG. 4. The axis of revolution C of the strain relief device 400 is aligned with the axis A of the connector 19. The cylinder cross section 401 is smaller at any point than the cross section at any point of the connector 19.

The free end 405 of the strain relief device 400 is chamfered or rounded so as to form an oblique surface 407 between the end 405 and a side wall 409 of the cylinder 401. This chamfered surface 407 makes it possible to avoid a sharp edge between the end 405 and the side wall 409 of the cylinder 401. Thus, the chamfer 407 reduces the potentially sharpness of the edge between the end 405 and the side wall 409 of the cylinder 401 which could damage or break the conductive wires 39a, 39b, 39c.

The side wall 409 of the cylinder 401 at the end 405 of the strain relief device 400 is provided with two deflection elements which are protuberances 413, 415 of cylindrical shape and respective axes of revolution P and P'. The protuberances 413, 415 are in particular positioned such that their axes of revolution P and P' are aligned with each other and such that the axes of revolution P and P' intersect the axis C of the cylinder 401 at the same point. Thus, the axes of revolution P, P' of the deflection elements 413, 415 are misaligned with the longitudinal axis C of the cylinder 401 of the device 400. Each protrusion 413, 415 has a junction 417, 419 with the side wall 409 of the cylinder 401. Each junction 417, 419 comprises a fillet 417a, 419a so as to round the transition between the side wall 409 and the respective lateral walls 413a, 415a of the protuberances 413, 415. The fillets 417a, 419a thus make it possible to reduce the concentration of constraint that would create a sharp angle and thus reduces the risk of damaging the wires. In a variant, the side wall 409 of the cylinder 401 could comprise only one protuberance 413. Thus, the chamfer 407 and the fillets 417a, 419a of the strain relief device 400 are all structural features that reduce the risk to damage the conductive wires 39a, 39b, 39c.

According to the fourth embodiment of the invention, the conductive wires 39a, 39b, 39c exit from their respective hypotubes 41a, 41b, 41c, to which they are welded, at the proximal end 31 of the connector 19. In order to deflect the conductive wires 39a, 39b, 39c, the conductive wires 39a, 39b, 39c form a loop around the lateral wall 413a of the protuberance 413 at the fillet 417a and at the chamfer 407, and another loop around the side wall 415a of the protuberance 415 at the fillet 419a and at the chamfer 407. The side walls 413a, 415a of the protuberances 413, 415 thus constitute deflection walls 413a, 415a of the reducing device. Alternatively, the conductive wires 39a, 39b, 39c may be wound several times around the side wall of each protuberance. In another variant, the number of turns of the conductive wires 39a, 39b, 39c around the deflection walls 413a, 415a of the protuberances 413, 415 may be different from one protuberance to the other. Advantageously, the conductive wires 39a, 39b, 39c and/or sections of the same conductive wire are superimposed on themselves at certain points during the assembly around the strain relief device 400.

This makes it possible to increase the friction between the superimposed portions of the conductive wires 39a, 39b, 39c and thus to improve their maintenance and holding in place.

The conductive wires 39a, 39b, 39c are then grouped into a multi-strand wire 40 at the end 405 of the strain relief device 400 of the connector 19 of the lead 21.

The arrangement of the conductive wires 39a, 39b, 39c around the deflection walls 413a, 415a of the strain relief device 400 allows the conductive wires 39*a*, 39*b*, 39*c* to be blocked when they are stressed in tension, that is to say, when the conductive wires 39*a*, 39*b*, 39*c* are stressed in tension by a force represented by an arrow F, they are locked on the strain relief device 200 against the deflection walls 413*a*, 415*a* of protuberances 413, 415. This allows in particular to reduce the mechanical stress experienced by the conductive wires 39*a*, 39*b*, 39*c* in tension and thus reduce the risk of rupture of the conductive wires 39*a*, 39*b*, 39*c* themselves and at the electrical connection with the hypotubes 41*a*, 41*b*, 41*c*.

Figures 5, 6, 7:
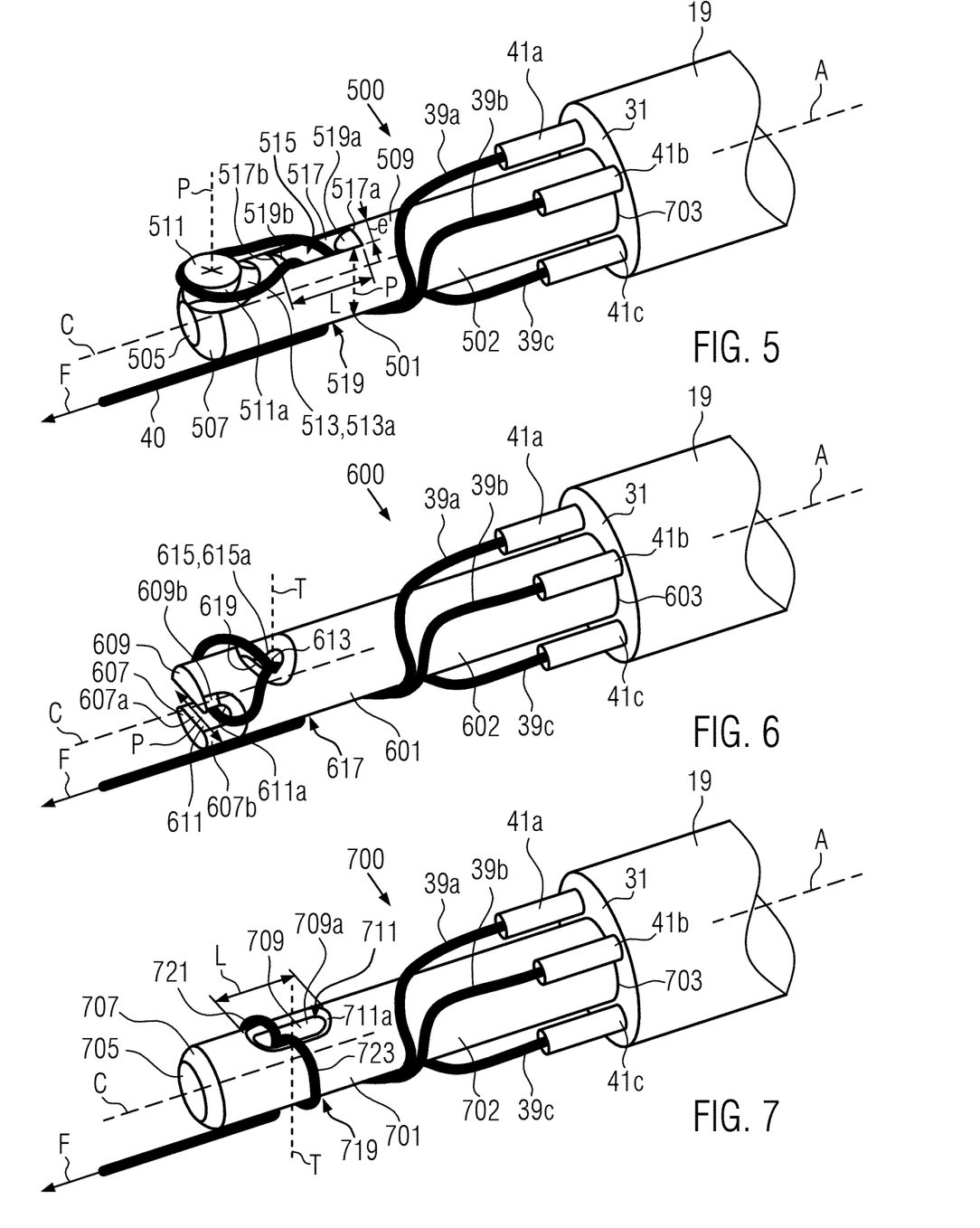
FIG. 5 represents a portion of the connector and a strain relief device according to a fifth embodiment of the present invention.
FIG. 6 represents a portion of the connector and a strain relief device according to a sixth embodiment of the present invention.
FIG. 7 shows a portion of the connector and a strain relief device according to a seventh embodiment of the present invention.

FIG. 5 illustrates a portion of the connector 19 and a strain relief device 500 according to a fifth embodiment of the present invention. The elements, in particular relating to the lead's connector, with the same numerical references already used for the description of FIGS. 1 to 4 will not be described again in detail, and reference is made to their descriptions above.

The strain relief device 500 of FIG. 5 according to the fifth embodiment has a shape of a right circular cylinder 501 of axis of revolution C. A first end 503 of the cylinder 501 is attached to the proximal end 31 of the connector 19. A second end 505 of the cylinder 501, opposite the end 503, is shown as a free end 505 in FIG. 5. The axis of revolution C of the strain relief device 500 is aligned with the axis A of the cylinder 19. The cross section 501 is smaller at any point than the cross section at any point of the connector 19.

The free end 505 of the strain relief device 500 is chamfered to form an oblique surface 507 between the end 405 and a side wall 509 of the cylinder 501. This chamfered surface 507 avoids a sharp edge between the end 505 and the side wall 509 of the cylinder 501. Thus, the chamfer 507 makes it possible to reduce the potential sharpness of the edge between the end 505 and the side wall 509 of the cylinder 501 which could damage or break the conductive wires 39*a*, 39*b*, 39*c*.

According to the fifth embodiment, the side wall 509 of the cylinder 501 at the end 505 of the strain relief device 400 is provided with a first deflection element, here a cylindrical protuberance 511 with lateral deflection wall 551*a* and axis of revolution P. The protuberance 511 is positioned adjacent the end 505 and such that its axis of revolution P perpendicularly intersects the axis C of the cylinder 501. Thus, the axis of revolution P of the first deflection element 511 is misaligned with the axis C of the cylinder 501 of the strain relief device 500. The deflection side wall 511*a* of the protuberance 511 has a junction 513 with the side wall 509 of the cylinder 501. The junction 513 is provided with a fillet 513*a* in order to round the edge between the side wall 509 and the protuberance 511. The fillet 513*a* thus makes it possible to reduce the stress concentration that a sharp angle would create at the junction 513. Alternatively, the side wall 509 of the cylinder 501 at the end 505 of the strain relief device 400 could also be provided on either side of the protuberance 511 of the protuberances 413, 415 according to the fourth embodiment. Thus, the chamfer 507 and the fillet 513 of the strain relief device 500 are as many characteristics that reduce the risk of damaging the conductive wires 39*a*, 39*b*, 39*c*.

The strain relief device 500 further comprises a second deflection element, here a through hole 515 near the protuberance 511, more precisely between the protuberance 511 and the end 503. The through hole 515, of length L and width e, has a depth p such that the through hole 515 passes through the cylinder 501 from one side, and in particular by intersecting the axis C of the cylinder 501. Therefore, the axis of the through hole 515 which extends along the depth p is misaligned with the axis C of the cylinder 501 The through hole 515 comprises two inputs 517, 519 opening on either side of the cylinder 501 such that the inputs 517, 519 are diametrically opposed to each other. The through hole 515 is positioned such that the inlet 517 of the hole 515 is aligned with the protuberance 511.

At the inlets 517, 519, each ridge 517*a*, 517*b* (only the ridge 517*a* is visible in FIG. 5) located between the width e of the through hole 515 and the side wall 509 is provided with a curve 519*a*, 519*b* that is, a rounded connecting surface 519*a*, 519*b* providing the junction between the width 1 of the through hole 515 and the side wall 509 so as to avoid a sharp angle which could damage the conductive wires 39*a*, 39*b*, 39*c*. Alternatively, the lengths L of each inlet 517, 519 of the through hole 515 may also be chamfered or rounded. According to the fifth embodiment, the conductive wires 39*a*, 39*b*, 39*c* are inserted through the inlet 519 into the through hole 515 and exit from the inlet 517 in a grouped method in a multi-stranded wire 40. The multi-stranded wire 40 is arranged in loop around the deflection wall 511*a* of the protuberance 511 and then inserted into the through hole 515 through the inlet 517. The multi-strand wire 40 then exits through the opposite inlet 519 and is aligned with the axis C of the cylinder 501 in a directed towards the end 505 of the cylinder 501. Thus, the conductive wires 39*a*, 39*b*, 39*c* are grouped into a multi-strand wire 40 at the end 505 of the strain relief device 500.

As a result, the conductive wires 39*a*, 39*b*, 39*c* are deflected by the first deflection member, i.e., the protuberance 511 and the second deflection member, the through hole 515 of the strain relief device 300 that the elements deviations 511, 515 make it possible to block the conductive wires 39*a*, 39*b*, 39*c* against the deflection wall 511*a* when they are stressed in tension by a force F. The respective axes P, p of the deflection elements 511, 515 extend perpendicularly to the longitudinal axis C of the strain relief device 500.

FIG. 6 illustrates a portion of the connector 19 and a strain relief device 600 according to a sixth embodiment of the present invention. The elements, in particular relating to the lead connector, with the same numerical references already used for the description of FIGS. 1 to 5 will not be described again in detail, and reference is made to their descriptions above.

The strain relief device 600 of FIG. 6 according to the sixth embodiment has the shape of a cylinder 601 of axis of revolution C and side wall 602.

A first end 603 of the cylinder 601 is attached to the proximal end 31 of the connector 19. A second end of the cylinder 601, opposite the end 603, is a free end. The axis of revolution C of the strain relief device 600 is aligned with the axis A of the connector 19. The cylinder cross section 601 is smaller at any point than the cross section at any point of the connector 19.

The free end of the cylinder 601 is provided with two protuberances 607, 609 which form between them a groove 611 which has a bottom 611*a*. The bottom 611*a* corresponds to the junction between a wall 607*a* of the protrusion 607 and a wall (not visible on the FIG. 6) of the protuberance 609 facing the wall 607*a*. The angles 607*b*, 609*b* of the walls 607*a*, 609*a* are chamfered or rounded so as to form an oblique surface which makes it possible to soften the junction with the groove 611. According to the sixth embodiment, the bottom 611*a* of the groove 611 corresponds to a deflection wall 611*a* of the strain relief device 600. The bottom 611*a* of the groove 611 extends longitudinally in a direction P which is perpendicular to the axis C of the strain relief device 600.

According to the sixth embodiment, the strain relief device 600 comprises towards the free end a deflection element, here a through hole 613 of axis T penetrating through the cylinder 601 such that there is an intersection between the axis T of the through hole 613 and the axis C of the 601. Thus, the axis T of the through hole 613 is misaligned with the axis C of the cylinder 601. The through hole 613 is dimensioned so that the conductive wires 39*a*, 39*b*, 39*c* can be inserted on both sides in the hole 613 by an entry 615 and an entry 617. Each entry 615, 617 of the hole 613 has a junction 615*a* (617*a* is not visible in FIG. 6) with the side wall 602 of the cylinder 601. The junctions 615*a*, 617*a* of the hole 613 are chamfered or rounded so as to soften the junction with the side wall 602 of cylinder 601 and to avoid damaging or breaking the conductive wires 39*a*, 39*b*, 39*c*. In addition, according to the sixth embodiment, the junctions 615*a*, 617*a* of the hole 613 are further chamfered on either side of a diameter D of the hole 613 so as to form a difference in height 619 on either side of the junctions 615*a*, 617*a*. This difference in height 619 makes it possible to improve the retention of the conductive wires 39*a*, 39*b*, 39*c* and to reduce the stresses on the conductive wires 39*a*, 39*b*, 39*c*. Alternatively, the through hole 613 could also be used in place of the through hole 515 described in the fifth embodiment described above with respect to FIG. 5.

In another variant, the side wall 602 of the cylinder 601 can be provided between the groove 611 and the through hole 613 with a protrusion around which the conductive wires 39*a*, 39*b*, 39*c* can be wound, for example provided with the protuberance 511 of the fifth embodiment.

According to the sixth embodiment, the conductive wires 39*a*, 39*b*, 39*c* are inserted through the entry 617 into the through hole 613 and exit from the through hole 613 through the inlet 615. The conductive wires 39*a*, 39*b*, 39*c* are then positioned along the direction P on the deflection wall 611*a* of the bottom of the groove 611. Thus, the conductive wires 39*a*, 39*b*, 39*c* are deflected perpendicularly with respect to the axis C of the cylinder 601 of the device 600, since the axis P of the deflection wall 611*a* is perpendicular to the axis C. The conductive wires 39*a*, 39*b*, 39*c* are then inserted through the entry 615 in the through hole 613 and out of the through hole 613 through the entry 617 in a multi-strand wire 40. Thus, in the case wherein the multi-strand wire 40 is pulled by a tensile force F, during the implantation of the lead for example, the conductive wires 39*a*, 39*b*, 39*c* are locked against the bottom 611*a* of the groove 611 delimited by the walls 607*a*, 609*a* of the protrusions 607, 609, which makes it possible to protect them from the stress in tension. This also makes it possible to prevent the conductive wires 39*a*, 39*b*, 39*c* from being pulled at the connection with the hypotubes 41*a*, 41*b*, 41*c*, which could break the welding between the conductors and the hypotubes and thus damage the electrical connection.

As a result, the conductive wires 39*a*, 39*b*, 39*c* are deflected by the groove 611*a* and the through hole 613 of the strain relief device 600 so that the deflection elements 611, 613 block the conductor wires 39*a*, 39*b*, 39*c* against the deflection wall 611*a* when they are stressed in tension by a force F.

FIG. 7 illustrates a portion of the connector 19 and a strain relief device 700 according to a seventh embodiment of the present invention. The elements, in particular relating to the lead connector, with the same numerical references already used for the description of FIGS. 1 to 6 will not be described again in detail, and reference is made to their descriptions above.

The strain relief device 700 of FIG. 7 according to the seventh embodiment has a shape of right circular cylinder 701 of axis of revolution C and side wall 702. A first end 703 of the cylinder 701 is attached to the proximal end 31 of the connector 19. A second end 705 of the cylinder 701, opposite the end 703, is shown as a free end 705 in FIG. 7. The axis of revolution C of the strain relief device 700 is aligned with the axis A of the connector 19. The cylinder cross section 701 is smaller at any point than the cross section at any point of the connector 19.

The free end 705 of the strain relief device 700 is chamfered or rounded so as to form an oblique surface 707 between the end 705 and the side wall 702 of the cylinder 701. This chamfered surface 707 makes it possible to avoid a sharp edge by softening the edge between the end 705 and the side wall 709 of the cylinder 701. Thus, the chamfer 707 makes it possible to avoid damaging or breaking the conductive wires 39*a*, 39*b*, 39*c*.

The cylinder 701 of the strain relief device 700 comprises a deflection element, here an oblong hole 709 passing through the cylinder 701 on either side so that the axis T which extends along the depth of the hole 709 intersects the axis C of the cylinder 701. Therefore, the through hole 709 includes an inner deflection wall 709*a* which extends along the axis T of the oblong hole 709, that is to say perpendicular to the axis C of the cylinder 701 of the device 700. The through hole 709 is provided with two inlets (or outlets) 711, 719 at the side wall 702, which are diametrically opposed to each other. The through hole 709 is positioned so that the longest length L of the through-hole 709 is parallel to the axis C of the cylinder 701.

Each inlet 711, 719 of the through hole 709 has a junction 711*a* (719*a* is not visible in FIG. 7) with the side wall 702 of the cylinder 701. The junctions 711*a* of the through hole 709 are chamfered or rounded to soften the junction with the side wall 702 of the cylinder 701 and to avoid damaging or breaking the conductors 39*a*, 39*b*, 39*c*.

According to the seventh embodiment, the conductive wires 39*a*, 39*b*, 39*c* are inserted through the inlet 719 into the through-hole 709 and exit from the through-hole 709 through the inlet 711. They are then wound in an opposite direction on a cylinder half-turn 701 to be introduced again into the through-hole 709 through the inlet 719. The leads 39*a*, 39*b*, 39*c* are then extended from the through-hole 709 through the inlet 719 and directed to the end 705 of the strain relief device 700.

Thus, the conductive wires 39*a*, 39*b*, 39*c* are arranged in two loops 721, 723 around the oblong hole 709 of the cylinder 701. As a result, when the conductive wires 39*a*, 39*b*, 39*c* are pulled by a tensile force F, when the implantation of the lead, for example, the loops 721, 723 of conductive wires are locked in particular against an inner wall 709*a* of the oblong hole 709 called deflection wall 709*a*, which allows protecting them from tensile stress. This thus makes it possible to prevent the conductive wires 39*a*, 39*b*, 39*c* from being pulled at the connection with the hypotubes 41*a*, 41*b*, 41*c*, which could break the weld between the conductive wires and the hypotubes and thus damage the electrical connection.

Figure 8:
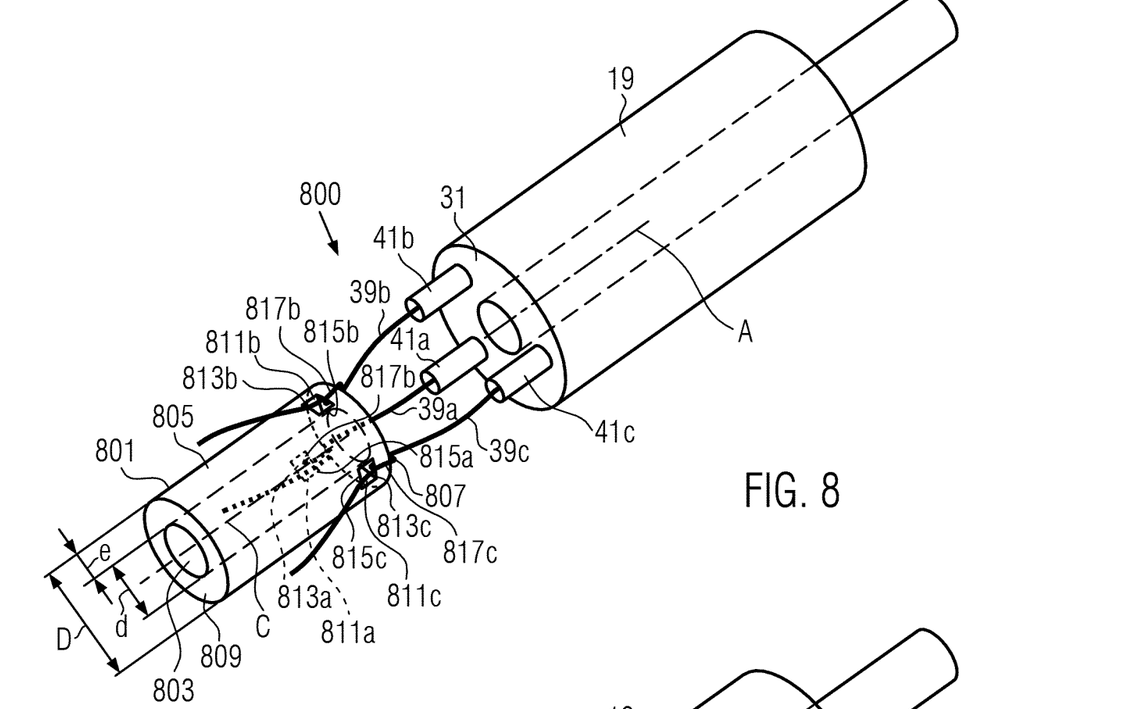
FIG. 8 represents a portion of the connector and a strain relief device according to an eighth embodiment of the present invention

FIG. 8 illustrates a portion of the connector 19 and a strain relief device 800 according to an eighth embodiment of the present invention. The elements, in particular relating to the lead connector, with the same numerical references already used for the description of FIGS. 1 to 7 will not be described again in detail, and reference is made to their descriptions above.

The strain relief device 800 is configured to accommodate different types of leads, such as multi-lumen leads, leads with a coaxial or coradial structure, etc. According to the eighth embodiment, the strain relief device 800 is attached to the proximal end 31 of the connector 19. However, in order to more easily illustrate the structure of the strain relief device 800, FIG. 8 shows the strain relief device 800 detached from the connector 19.

The strain relief device 800 is in the form of a tube 801 comprising a hollow portion 803 of axis C. The strain relief device 800 is positioned so that the axis C is aligned with the axis A of the connector 19. The tube 801 comprises a side wall 805 which extends along the axis C between an end 807 and one end 809. The end 807 of the tube 801 faces the end 31 of the connector 19. The hollow portion 803, of circular section, has a diameter d, also called internal diameter of the tube 801. The tube 801 has an external diameter D, such that there is a thickness e between the outer diameter D and the inner diameter d.

At the end 807, the tube 801 is provided with deflection elements, which are in the same number as the conductive wires 39a, 39b, 39c. Thus, according to the eighth embodiment illustrated in FIG. 8, the tube 801 is provided with three through-holes 811a, 811b, 811c each sized to receive a conductive wire 39a, 39b, 39c. The through holes 811a, 811b, 811c pass through the sidewall 805 up to the hollow portion 803. As a result, the through holes 811a, 811b, 811c have a depth equivalent to the thickness e. Each of the holes 811a, 811b, 811c comprises a first inlet 813a, 813b, 813c flushing with the side wall 805 and a second input 815a, 815b, 815c opening on the hollow portion 803.

According to the seventh embodiment, the conductive wires 39a, 39b, 39c are introduced into the hollow portion 803 by the end 807 and then each conductor wire 39a, 39b, 39c is inserted into the corresponding through hole 811a, 811b, 811c by the inlet 815a, 815b, 815c and exits through the inlet 813a, 813b, 813c. Each conductive wire 39a, 39b, 39c is again inserted into the hollow portion 803 by the end 807 so as to form a loop 817a, 817b, 817c. Each conductive wire 39a, 39b, 39c is then inserted into the corresponding through hole 811a, 811b, 811c through the inlet 815a, 815b, 815c and exits through the inlet 813a, 813b, 813c. In this method, each conductive wire 39a, 39b, 39c is individually protected from tensile stress because when a conductive wire 39a, 39b, 39c is pulled, this causes a locking of the loop 817a, 817b, 817c around the 807 end of the tube 801. This thus prevents the conductive wires 39a, 39b, 39c from being stressed in tension at the connection with the hypotubes 41a, 41b, 41c, which could break the weld between the conductive wires and the hypotubes and thus damage the electrical connection.

Figure 9:
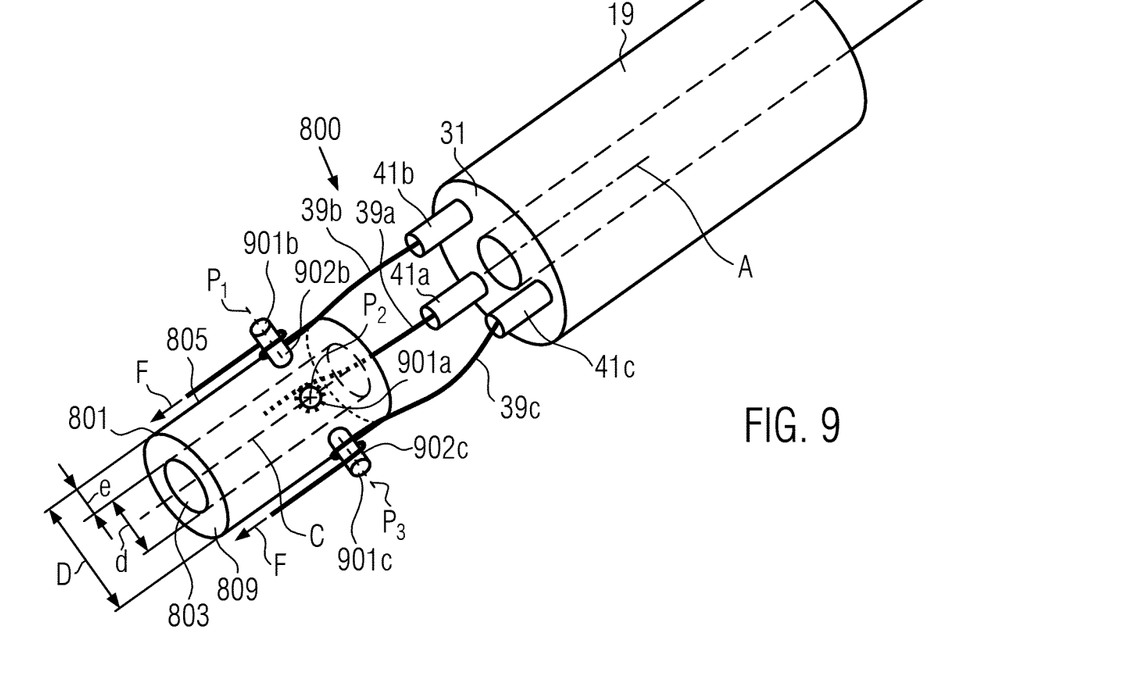
FIG. 9 shows a portion of the connector and a strain relief device according to a ninth embodiment of the present invention.

FIG. 9 illustrates a portion of the connector 19 and a strain relief device 900 according to a ninth embodiment of the present invention. Elements with the same numerical references already used for the description of FIGS. 1-8 will not be described again in detail, and reference is made to their descriptions above.

Similarly to the eighth embodiment, the strain relief device 900 of the ninth embodiment is configured to accommodate different types of leads, such as multi-lumen leads, leads with a coaxial or coradial structure, etc. Thus only the structural elements which differ from those already described for the strain relief device 800 will be described.

Unlike the strain relief device 800 described in FIG. 8, the tube 801 of the strain relief device 900 does not include through holes as deflection elements but cylindrical protuberances 901a, 901b, 901c at the end 807 of the tube 801.

These cylindrical protuberances 901a, 901b, 901c protrude from the side wall 805 of the cylinder 801 so that their respective axes of revolution P1, P2, P3 intersect the axis C of the cylinder 801 at the same point. Thus, the side walls 902a, 902b, 902c protuberances 901a, 901b, 901c extend perpendicularly to the side wall 805 of the cylinder 801. In the ninth embodiment, the side walls 902a, 902b, 902c protuberances 901a, 901b, 901c are the walls of deflection 902a, 902b, 902c of the strain relief device 900.

According to the ninth embodiment, the conductive wires 39a, 39b, 39c are each arranged around the side walls 902a, 902b, 902c of the protuberances 901a, 901b, 901c of the tube 801. Thus, in the case wherein the conductive wires 39a, 39b, 39c are pulled by a tensile F, during the implantation of the lead for example, each conductive wire 39a, 39b, 39c are locked around the respective protuberance 901a, 901b, 901c which allows to protect them from the stress in tension. This thus makes it possible to prevent the conductive wires 39a, 39b, 39c from being pulled at the connection with the hypotubes 41a, 41b, 41c, which could break the weld between the conductive wires and the hypotubes and thus damage the electrical connection.

The described embodiments are merely possible configurations and it should be borne in mind that the individual features of the nine embodiments can be combined with each other or provided independently of one another. In addition, the geometries shown in FIGS. 2 to 9 can be varied without departing from the concepts of the inventions. In a variant, shown in FIG. 3 and applicable to all embodiments, each of the conductive wires can first be welded to an intermediate hypotube of smaller diameter than the hypotube of the connector before being inserted into the hypotube of the conductor. In particular, for conductive wire diameters smaller than 150 micrometers, the use of intermediate hypotubes, as described in the embodiment of FIG. 3, can improve the longevity of the lead.

What is claimed is:
1. An implantable lead comprising:
at least one conductive wire; and
a connector having a first end and a second end, the connector configured to be connected to an implantable medical device, such as a cardiac stimulation, a defibrillation or a neuromodulation device at the first end, and further comprising a strain relief device integrated with the connector, the connector having an axis extending between the first end and the second end, and the strain relief device extending longitudinally along an axis away from the second end of the connector and essentially parallel to the axis of the connector, the strain relief device comprising a through hole at an end of the strain relief device, wherein the through hole comprises a deflecting wall,
wherein the conductive wire is deflected by the deflecting wall of the strain relief device such that the conductive wire is blocked against the deflecting wall when the conductive wire is stressed in tension, and the deflecting wall extends along an axis which is misaligned with the axis of the strain relief device, and
wherein the conductive wire is introduced at least twice through the through hole so that the conductive wire is arranged in a loop around a portion of the strain relief device.
2. The implantable lead of claim 1, wherein at least one section of the conductive wire is arranged in a loop around the deflection wall of a protuberance projecting from an outer surface of the strain relief device.

3. The implantable lead of claim 2, wherein the protuberance has a cylindrical shape and an axis of revolution misaligned with the longitudinal axis of the strain relief device.

4. The implantable lead of claim 1, wherein the deflecting wall extends along an axis which is misaligned with the axis of the strain relief device so as to form a right angle, especially a right angle at plus or minus 10 degrees.

5. The implantable lead of claim 1, wherein at least two sections of the conductive wire partially or totally overlap.

6. The implantable lead of claim 1, comprising a plurality of conductive wires such that each conductive wire is deflected by the strain relief device such that the conductive wires are blocked against the deflecting wall when the conductive wires are stressed in tension.

7. The implantable lead of claim 6, wherein the conductive wires exit from one end of the connector separately from one another and are grouped into a multi-stranded wire by their arrangement around the strain relief device.

8. The implantable lead of claim 1, wherein the strain relief device is attached to one end of the connector by at least one of gluing, by interlocking, snap connection or one or more fasteners.

9. An implantable medical device for cardiac pacing, defibrillation, or neuromodulation comprising:
an implantable lead comprising a connector, a strain relief device, and at least one conductive wire electrically connected to the connector, the connector having a first end and a second end, the connector having an axis extending between the first end and the second end, and the connector configured to be connected to the implantable medical device at the first end,
wherein the strain relief device is integrated with the connector and extends longitudinally along an axis away from the second end of the connector and essentially parallel to the axis of the connector, the strain relief device comprising a through hole at an end of the strain relief device, and wherein the through hole comprises a deflecting wall, the connector and the strain relief device configured to be housed in the implantable medical device, and
wherein the conductive wire is deflected by the deflecting wall of the strain relief device such that the deflecting wall of the strain relief device blocks the conductive wire when the conductive wire is stressed in tension, and the deflecting wall extends along an axis which is misaligned with the axis of the strain relief device, and
wherein the conductive wire is introduced at least twice through the through hole so that the conductive wire is arranged in a loop around a portion of the strain relief device.

10. The implantable medical device of claim 9, wherein at least one section of the conductive wire is arranged in a loop around the deflection wall of a protuberance projecting from an outer surface of the strain relief device.

11. The implantable medical device of claim 10, wherein the protuberance has a cylindrical shape and an axis of revolution misaligned with the longitudinal axis of the strain relief device.

12. The implantable medical device of claim 9, wherein the deflecting wall extends along an axis which is misaligned with the longitudinal axis of the strain relief device so as to form a right angle, especially a right angle at plus or minus 10 degrees.

13. A method of manufacturing an implantable lead configured to be connected by one or more conductive wires and a connector to an implantable medical device such as a cardiac stimulation, defibrillation or neuromodulation device, the connector having a first end and a second end, the connector having an axis extending between the first end and the second end, and the connector configured to be connected to the implantable medical device at the first end, the implantable lead further comprising a strain relief device integrated with the connector at the second end of the connector, the strain relief device extending longitudinally away from the second end of the connector and essentially parallel to the axis of the connector, the strain relief device comprising a through hole at an end of the strain relief device, wherein the through hole comprises a deflecting wall, the method comprising:
deflecting the one or more conductive wires by the strain relief device so as to arrange the one or more conductive wires of the connector around the deflecting wall which extends along an axis which is misaligned with the axis of the strain relief device,
wherein when the at least one conductive wire is stressed in tension, the at least one conductive wire is locked against the deflecting wall of the strain relief device, and
wherein the at least one conductive wire is introduced at least twice through the through hole so that the at least one conductive wire is arranged in a loop around a portion of the strain relief device.

14. The method of claim 13, further comprising, arranging at least one section of the conductive wire in a loop around the deflection wall of a protuberance projecting from an outer surface of the strain relief device.

* * * * *